US006676619B2

(12) United States Patent
Arden (10) Patent No.: US 6,676,619 B2
(45) Date of Patent: Jan. 13, 2004

(54) METHOD AND APPARATUS FOR SUPPORTING A BODY PART

(76) Inventor: Wayne R. Arden, P.O. Box 775972, Steamboat Springs, CO (US) 80477

( * ) Notice: Subject to any disclaimer, the term of this patent is extended or adjusted under 35 U.S.C. 154(b) by 24 days.

(21) Appl. No.: 09/792,527

(22) Filed: Feb. 23, 2001

(65) Prior Publication Data

US 2002/0120222 A1 Aug. 29, 2002

(51) Int. Cl.[7] ................................................ A61F 5/00
(52) U.S. Cl. .................... 602/8; 602/5; 602/60
(58) Field of Search ............................. 602/18–20, 5–8, 602/1, 23, 27–29, 60–62, 65; 128/873–875, 845–846, 869–870, 882; 2/44, 45, 69, 455–456, 903; 604/289; 119/725–726, 814, 816–818, 850, 856–857

(56) References Cited

U.S. PATENT DOCUMENTS

| | | | | |
|---|---|---|---|---|
| 4,425,912 A | * | 1/1984 | Harper ........................ | 602/26 |
| 4,445,505 A | * | 5/1984 | Labour et al. ................ | 602/26 |
| 5,248,292 A | * | 9/1993 | Holland ........................ | 602/6 |
| 5,709,648 A | * | 1/1998 | Webb ............................ | 602/19 |
| 5,980,474 A | * | 11/1999 | Darcey ........................... | 602/5 |
| 6,007,505 A | * | 12/1999 | Grim et al. ..................... | 602/6 |
| 6,267,083 B1 | * | 7/2001 | Chimienti .................... | 118/850 |

* cited by examiner

Primary Examiner—Nicholas D. Lucchesi
Assistant Examiner—Lalita M Hamilton
(74) Attorney, Agent, or Firm—Timothy J. Martin; Michael R. Henson; Rebecca A. Gegick (57) ABSTRACT

A method and apparatus for supporting a body part utilizes an external splint to form a brace. The splint includes an elongated sheath connected and an elongated support piece placed in the interior of the sheath. The support piece is formed of a stiff material and is shorter that the sheath in length so that it can move relative to the sheath. The support piece is preferably formed of a composite material. One or more splints may be used to form a brace. Here, a mounting piece secures the splint(s) and mounts on the body part. A casing may be used over the brace. Alternatively, the splints can be formed in the casing. The method then involves the steps of supporting the body part with the splint(s) and brace described above.

37 Claims, 5 Drawing Sheets

METHOD AND APPARATUS FOR SUPPORTING A BODY PART

FIELD OF THE INVENTION

The present invention is broadly directed to the medical and veterinary field. More particular, the present invention concerns a apparatus, such as splints, braces, temporary casts and the like. Specifically, the present invention concerns a brace which can mounted alongside a body part in order to provide protective support as well as a method of implementing such a brace and supporting the body part against injury.

BACKGROUND OF THE INVENTION

Locomotion is a cardinal sign of animal life including humans as well as the lower animal forms. In higher living organisms, movement is typically accomplished by appendages such as legs and arms attached to a trunk or body portion of the animal. Active movement exposes the animal to various forms of trauma, particularly to the bones and joints. Such trauma can include strains, sprains, bone cracking or breaking and the like. Furthermore, natural aging processes deteriorate animal body structures with bones and joints being particularly susceptible to age-related deterioration. Even when injured or advanced in age, animals typically require some level of movement for meaningful life and often for survival.

It is known to provide auxiliary support for various body parts of both humans and domestic animals. For example, in the case of a bone crack or break, the bone may be set and a rigid cast placed around the body part corresponding to the broken or cracked bone so as to inhibit any movement during the healing process. Such casts are typically uncomfortable and cumbersome and act to severely restrict movement of the body part. As an alternative to casts, rigidifying structures in the form of rod-like or stick braces are used. Here, also, the goals are to provide auxiliary support to the body part and to severely restrict the motion of the body part as a form of protection against further injury and to promote healing. In the case of a splint, a rigidifying structure such as a rod, slate or other elongated rigid piece is placed alongside the body part, typically on each side of the joint, and mounted in position so as to restrict motion about the joint or about a fracture. The mounting of the splint is usually by a flexible wrap which, in some instances, may be an elastic support bandage or the like.

In some instances, it is sufficient to provide auxiliary support to the body part by means of a flexible resilient member such as an elastic casing, elastic wrap and the like. In the case of an elastic wrap, an elongated strip of elastic cloth is typically wound circumferentially around the body part so as to encase the body part in the mass of flexible material. Alternatively, the elastic device may be formed as a tube-like sheath that is slid onto the body part so as to encircle the body part thereby providing lateral stability. In either case, the resilient devices support the body part so as to resist undesired bending. The resilient nature of the material, while not as rigidifying as a splint or cast, has been found to supplement the body's own support structure so as to reduce pain during movement and reduce the likelihood of additional injury.

Auxiliary supports are used both as a treatment device as well as a prophylactic device. During treatment, such devices help prevent movement and promote the healing process as noted above. As a prophylactic device, such devices provide auxiliary support prior to any injury so as to reduce the likelihood of injury by augmenting the body's support framework and musculature. For example, many persons engaged in athletic endeavors will wear elastic knee braces, elbow braces, wrist braces, ankle braces and the like during the athletic activity to reduce the likelihood of injury during movement. Indeed, it is known that many athletes partially immobilize an ankle joint by adhesive taping to allow flexion of the foot with reduced risks of lateral movement that might cause a strain or sprain.

Despite the protection provided by elastic support devices, the same often provide inadequate support for the injured body part or inadequate protection against injury as a prophylactic approach. Braces and casts, on the other hand, restrict movement to a degree that prevents meaningful sufficient movement during athletic activities. Accordingly, there is a need for an apparatus that bridges the gap between braces and casts on one hand, and elastic bandages and casings on the other. There is a need for such devices that have greater support against lateral motion of the body part while still allowing sufficient flexibility of the body part for active movement. There is a further need for a method of supporting body parts for movement while substantially resisting lateral deflection of the body part that could permit injury.

SUMMARY OF THE INVENTION

It is an object of the present invention to provide a new and useful splint or brace adapted to support a selected body part of a person or animal.

It is a further object of the present invention to provide a new and useful splint or brace which may be used on injured or weakened animal body parts.

It is a further object of the present invention to provide a new and useful splint or brace which supports the injured or weakened body part while still allowing some degree motion the injured or weakened body part.

It is still a further object of the present invention to provide a new and useful splint or brace in which the support piece of the brace floats within the confines of the flexible portion of the brace to provide flexibly stiff support for an injured or weakened body part.

It is still a further object of the present invention to provide an easily releasable splint or brace.

It is yet another object of the present invention to provide an adjustable splint or brace that resists impact forces and is light in weight.

A still further object of the present invention is to provide a brace that may enhance athletic performance of the wearer.

According to the present invention, then, a brace is adapted for use on a body to externally support a selected body part having a long axis. Broadly, the brace includes a mounting piece that is operative to releasably secure in a mounted state to a portion of the body at a location proximate to the selected body part. An elongated sheath is formed of a first flexible material and has a sheath interior. A first end of the sheath is connected to the mounting piece at a junction and has a second end opposite the first end. An elongated support piece is disposed within the interior of the sheath. The support piece has a length that is less than the length of the interior of the sheath so that the support piece may move relative to the sheath in the longitudinal direction. The sheath and the support piece are thus configured to extend alongside the selected body part when in the mounted state. If desired, the support piece can have a width that is slightly less than the width of the sheath interior.

The mounting piece of the invention is preferably constructed of a flexible material, such as nylon. The mounting piece can have both an elastic portion and an inelastic portion. This mounting piece may be formed as an elongated strip of material to extend around the selected body parts. Cooperating fasteners are provided at opposite ends of the mounting piece in order to secure these ends together in the mounted state. Preferably, the brace of the present invention includes a plurality of sheaths each having a support piece disposed therein, dimensioned as set forth above. One of the support pieces can be a different width than another of the support pieces. In any event, the sheaths are preferably in parallel spaced relation to one another and have first ends secured to the mounting piece and second, free ends opposite the first ends. The mounting piece is an inelastic between the junctions and have elastic portions on opposite ends.

The support piece of the present invention is preferably constructed of a composite material. The composite material is selected from a group consisting of aramid compounds, kevlar, graphite, plastics (such as polyethylene) and Teflon. In any event, it should be a lubricous material. The support piece may be constructed of two different fibers woven together, such as a carbon/kevlar blend. This woven construction can then be impregnated with a resin. In any event, the support piece may be coated with a hydrophobic material so as to resist water and sweat.

In a simplified form of the present invention, a splint is provided for use on a body to external support a selected body part along its long axis. The splint comprises an elongated sheet formed of flexible material and having a sheath interior with a first length. An elongated support piece formed of a stiff yet resilient material is received in the sheath interior and has a second length that is less than the length of the sheath. With this construction, the support piece may move relative to the sheath within the interior. Here again the support piece is constructed as described above. A mounting piece may be included to releasably secure the sheath in the support piece along side the selected body part and parallel to the long axis thereof.

The present invention also is directed to a system adapted for use on a body to externally support a selected body part having a long axis. This system includes a brace, as described above, formed of one or more splints, as described above. The system also includes an elastic casing that is sized and adapted to extend over the selected body part in a retaining position so that it is operative in retaining position to encase a major portion of the sheath and the support piece when in the mounted state. Here, again, a plurality of sheathes and support pieces are preferably provided with the sheaths (and their respective support pieces) being in parallel spaced relation to one another. The support pieces are constructed again of composite materials as described above.

The present invention also contemplates an improvement to elastic braces. The improvement includes an elongated sheath formed in the elastic casing and constructed of a flexible material having a sheath interior having a first length and elongated support piece formed of a stiff material received in the sheath interior. Here, again, the length of the support piece is less than the length of the sheath so that the support piece may move, i.e. "float", relative to the interior of the sheath. The stiff material is preferably constructed as a woven composite, noted above. In this improvement, one or more elongated sheaths may be provided and may either be permanently affixed to the elastic casing or otherwise mounted thereby. Preferably a plurality of sheaths and corresponding support pieces are connected to the elastic casing at desired locations.

The present invention finally is directed to a method that is accomplished by the structures described above. Therefore, the method of the present invention externally supports a selected body part having a long axis. The method includes a first step of providing a splint that includes a sheath of flexible material and a support piece disposed in the interior of the sheath. Next, the method includes the step of placing the splint alongside the selected body part in an orientation that is parallel to the long axis thereof. Finally, the splint is secured in a mounted state in a manner such that, during movement, the support piece can reciprocate in a longitudinal direction within the interior of the sheath.

The method also may include the step of providing a plurality of these splints, placing each of the splints alongside the selective body part in an orientation that is parallel to the long axis and securing each of the splints in a mounted state, in a manner such that, during movement, each support piece can reciprocate in a longitudinal direction within the interior of its respective sheath. The method can also include the step of orienting the splints in spaced-apart relation to one another, and this method can also include equiangularly spacing of the splints around the selected body part. The step of securing the splint can be accomplished by utilizing a non-stretchable mounting strip extending around the selected body part or, alternatively, utilizing a mounting strip that includes an elastic portion.

These and other objects of the present invention will become more readily appreciated and understood from a consideration of the following detailed description of the exemplary embodiment of the present invention when taken together with the accompanying drawings, in which:

DETAILED DESCRIPTION OF THE EXEMPLARY EMBODIMENTS

The present invention is broadly directed to medical and veterinary devices, such as orthopedic devices that are used to support a body part. In addition, the present invention is directed to a splint which can be incorporated or used as a support device for various body parts. The invention also serves to provide impact protection. Finally, the present invention is also directed to a method of supporting the body part against the risk of injury or additional injury. Accordingly, when used herein, the term "body part" can refer to any portion of an animal's body. Here, also, the term "animal" includes human as well as non-human animals.

Figure 1:
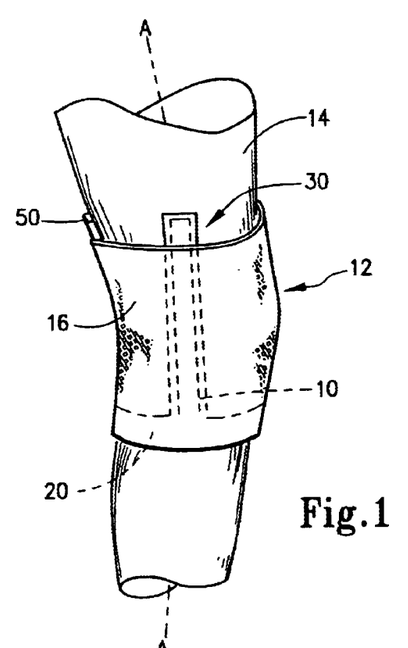
FIG. 1 is a perspective view of a brace according to a first exemplary embodiment of the present invention with this brace being shown secured around the knee joint a human leg.

With reference first to FIG. 1, brace 10 according to a first exemplary embodiment of the present invention is shown secured in a mounted state at the knee joint 12 of a human leg 14. Leg 14 has a long axis "A". Brace 10 is mounted about knee joint 12 and is supplemented by an auxiliary elastic support 16 of a type known in the prior art.

Figure 2:
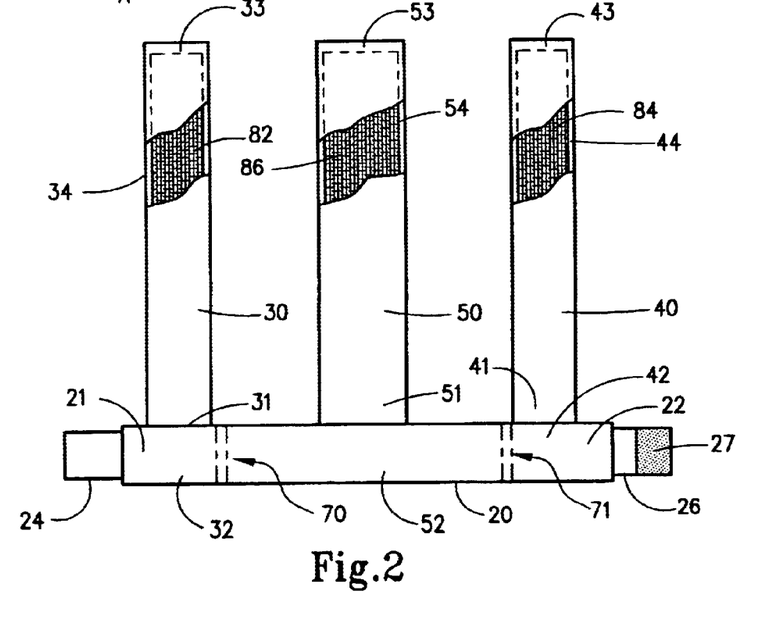
FIG. 2 is a front view in elevation, partially broken away, showing the first exemplary embodiment of a brace according to the present invention.

With reference now to FIG. 2, brace 10 is shown in greater detail. Here, brace 10 includes an elongated mounting piece in the form of a sleeve 20 fabricated out of a flexible fabric material, such as nylon. Sleeve 20 is operative to be releasably secured in a mounted state to a portion of the body at a location proximate to the selected body part. A plurality of elongated sheaths 30, 40 and 50 are connected to sleeve 20 and are oriented in generally parallel spaced-apart relation to one another. Sheath 30 has a first end portion 31 secured to sleeve 20 at a junction 32 located proximately to a first end portion 21 of sleeve 20. Similarly, sheath 40 has a first end portion 41 connected at a junction 42 that is located proximately to second end portion 22 of sleeve 20. Sheath 50 has a first end portion 51 secured to sleeve 20 at a junction 52 that is located in a medial portion of sleeve 20 between end portions 21 and 22 thereof. Each of sheaths 30, 40 and 50 are in the form of an elongated sleeve constructed of a flexible fabric material, such as nylon and the like. Sheaths 30, 40 and 50 have second end portions 33, 43 and 53, respectively, opposite their respective first end portions 31, 41 and 51.

Sleeve 20 is adapted to extend circumferentially around a body part to mount brace 10 thereto so that sheaths 30, 40 and 50 can be positioned laterally alongside the body part and, with reference to FIG. 1, it may be seen that these sheaths 30 and 50 (as well as sheath 40, not shown) are oriented parallel to the long axis "A" of the body part and positioned alongside the exterior surface of the body part. With reference again to FIG. 2, it may be seen that a pair of elastic strips 24 and 26 extend out of sleeve 20 and project oppositely one another. As described below, strips 24 and 26 are provided with matable fasteners so as to connect to one another.

Figure 3:
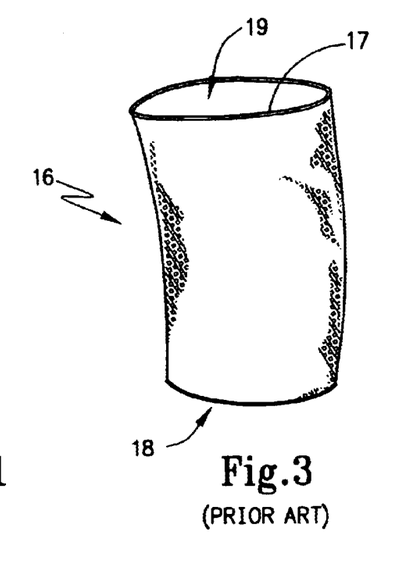
FIG. 3 is a perspective view of an auxiliary elastic sheath that may be employed with the brace shown in FIG. 2.
Figure 4:
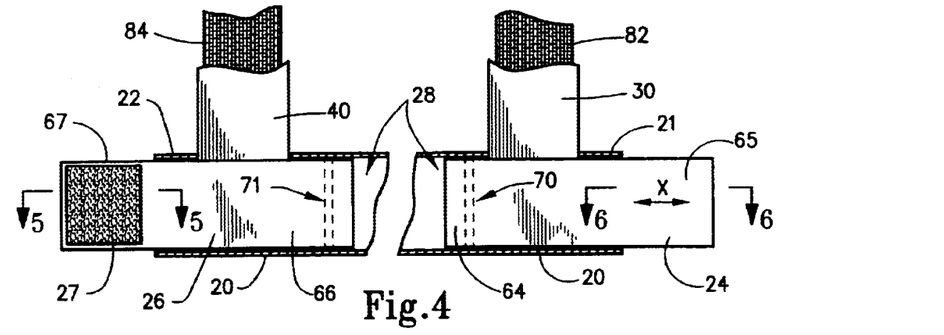
FIG. 4 is a front view in partial cross-section showing the lower portion of the brace of FIG. 2.
Figure 5:
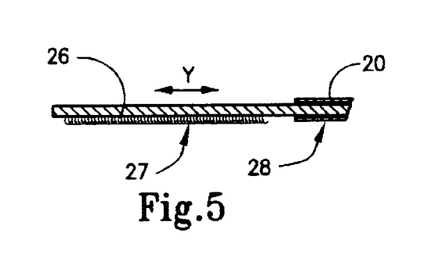
FIG. 5 is a cross-sectional view taken about lines 5—5 of FIG. 4.
Figure 6:
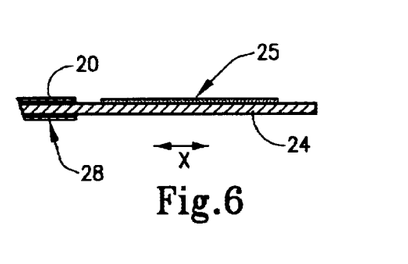
FIG. 6 is a cross-sectional view taken about lines 6—6 of FIG. 4.
Figure 10:
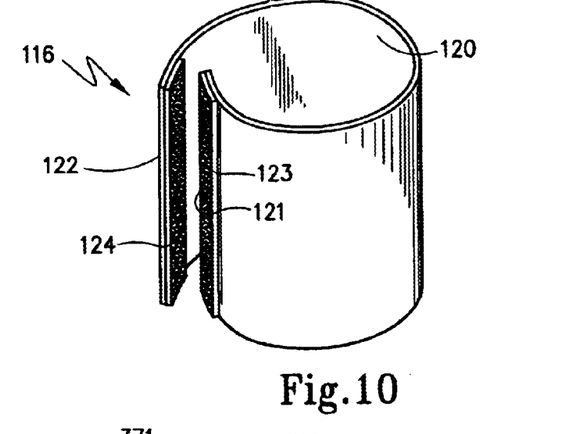
FIG. 10 is a perspective view of an alternative auxiliary elastic wrap used with the brace shown in FIG. 2.

To further enhance the use of brace 10, an elastic support 16 may be employed in a mounted position over brace 10, as is shown in FIG. 1. This elastic support 16 is of the known in the art, and is depicted in FIG. 3. Here, it may be seen that elastic support 16 is in the form of a tubular casing having a side wall 17 and opposite open ends 18 and 19. An alternative elastic support 116 is shown in FIG. 10 and is in the form of a band 120 of elastic material. Band 120 has opposite ends 121 and 122 that secure together by means of mating hook and fasteners 123 and 124 to form a tubular casing having opposite open ends 121 and 122. Thus, elastic support 116 may be secured around the mounted brace 10.

Returning, now, to FIGS. 2 and 4–8, it may be seen that elastic strip 24 is received in the interior 28 of sleeve 20 and, specifically, within first end portion 21 thereof. Elastic strip 24 has a first end portion 64 that is secured by stitching 70 to sleeve 20. Strip 24 has a free end portion 65 that protrudes longitudinally outwardly from first end portion 21 and is provided with fill-a-form elements 25 that forms one-half of a mating hook and loop fastener. Strip 24 can stretch back and forth as shown by arrows "X". It should be noted that strip 24 is not directly secured to sheath 30.

Similarly, elastic strip 26 extends into the interior 28 of sleeve 20 and, specifically, into second end portion 22 thereof. Strip 26 has a first end portion 66 that is secured by stitching 71 to sleeve 20 and a second end portion 67 that protrudes out of sleeve 20. End portion 67 is provided with loop elements 27 that forms a second half of a mating hook and loop fastener. Strip 26 expands and contracts in the direction of arrow "Y". Here, again, elastic 26 is not directly secured to sheath 40.

From the foregoing, it may be appreciated that sleeve 20 along with elastic strips 24 and 26 may be used as a mounting piece to secure brace 10 to a body part, as shown in FIG. 1. By providing elastic strips 24 and 26, a certain degree of adjustability for size is provided due to the stretchiness of strips 24 and 26 while filaform elements 25 and 27 provide a fastener to releasably connect end portions 65 and 67 together so that sleeve 20 extends circumferentially around the body part in a plane that is generally transverse to the long axis of the body part. Sleeve 20, while being flexible, is preferably not resilient but rather provides a non-expanding or contracting interconnection of sheaths 30, 40 and 50.

Figure 7:
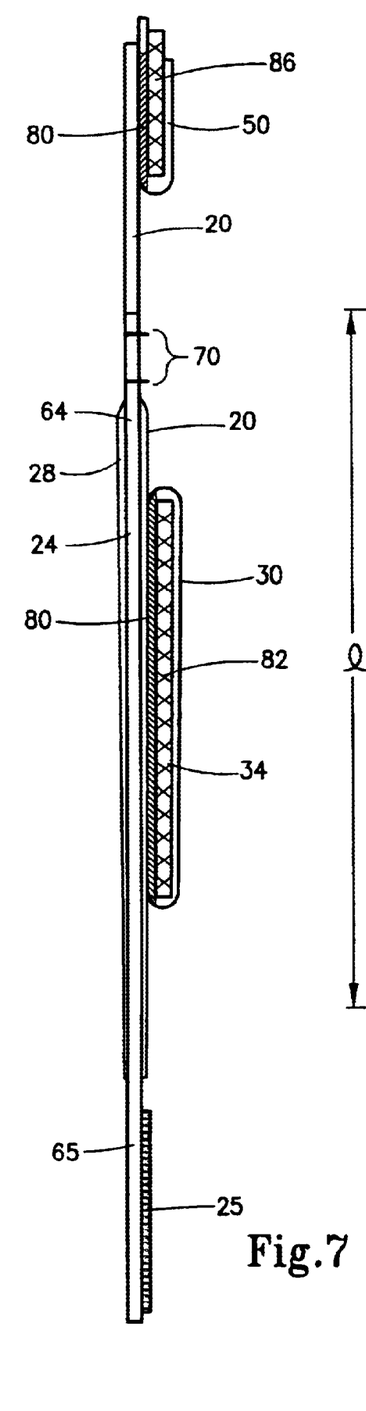
FIG. 7 is a top view in partial cross-section of a lower section of the brace shown in FIGS. 2 and 4–6.

Each of sheaths 30, 40 and 50, however, are directed secured to sleeve 20. For example, as is shown in FIG. 7, sheath 30 is adhered to sleeve 20 by a suitable adhesive 80 which, for example, may be a flexible fabric glue or other suitable adhesive. Naturally, any well-known attachment technique may be used to attach sheets 30, 40 and 50 to sleeve 20.

With reference to FIGS. 2, 4, 7 and 8, it may further be seen that each sheaths 30, 40 and 50 receive an elongated support piece that is formed of a stiff yet resilient material. Thus, for example, an elongated support piece in the form of a stiff strip 82 is received in the interior 34 of sheath 30. A similarly constructed strip 84 is floatingly received in interior 44 of sheath 40, and a similar strip 86 is floatingly received in the interior 54 of sheath 50. By this, it is meant that the strips can undergo sliding movement relative to their respective sheath. Strips 82, 84 and 86 respectively have first end portions that are secured to sleeve 20 at the respective junctions 32, 42 and 52. To this end, adhesive 80 acts both to secure these first end portions to sleeve 20 as well as to secure the first end portions of sheaths 30, 40 and 50 to sleeve 20. Thus, the majority of the length of each strip 82, 84 and 86 can move independently of the majority of the length of the respective sheath 30, 40 and 50. This floating construction increases the efficiency of the strips in their supportive function.

Figure 8:
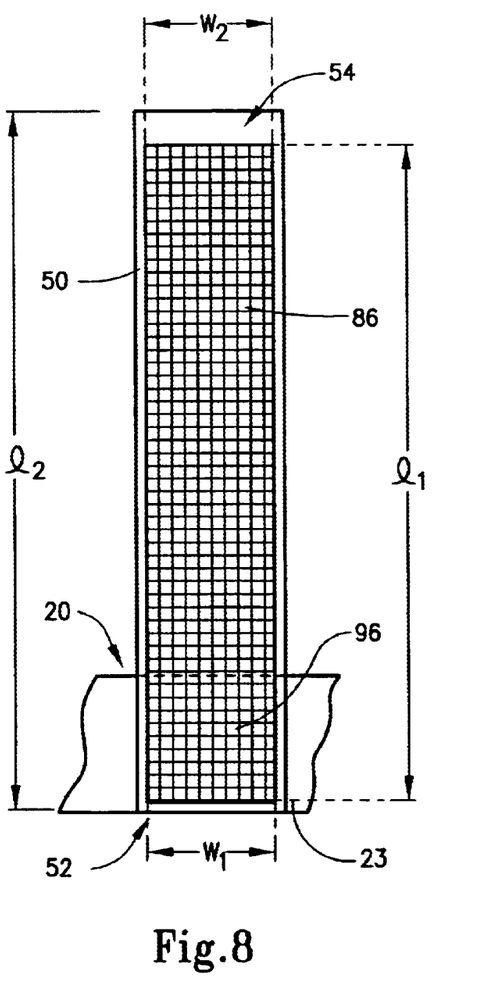
FIG. 8 is a front view in partial cross-section showing the elongated support piece and sleeve according to the first exemplary embodiment of the present invention.

The relationship of each of strips 82, 84 and 86 is comparable with its respect sheath 30, 40 and 50. Thus, for illustrative purposes, strip 86 is shown in FIG. 8 wherein it is received in the interior 54 of sheath 50. Here, first end portion 96 of strip 86 is secured at junction 52 to medial portion 23 of sleeve 20. Strip 86 has a length "$l_1$" and a width "$w_1$". Sheath 50, on the other hand, has a length "$l_2$" and a width "$w_2$". According to the exemplary embodiment of the present invention, it should be understood that $l_2$ is greater than $l_1$, likewise, $w_2$ is greater than $w_1$. With this construction, the interior 54 of sheath 50 is both wider and longer than strip 86 so that strip 86 may undergo both longitudinal and lateral sliding, at least to a small degree, within the interior of its respective sheath 50. Similarly, strip 82 is dimensioned slightly smaller than the interior dimension of sheath 30, and strip 84 is dimensioned slightly smaller than the interior 44 of sheath 40. Moreover, it should be noted that, while the length of strips 82, 84 and 86 are preferably the same, it is also preferred that the width of strip 86 is greater than the width of each of strips 82 and 84 with the width of strips 82 and 84 being the same. This construction is believed to be superior where brace 10 is used as a knee brace with sheath 50 and strip 86 extending along the back side of the knee with sheaths 30 and 40 along with their corresponding strips 82 and 84 being located laterally to the side of knee on opposite sides thereof.

According to the present invention, it is important that the support pieces, in the form of strips 82, 84 and 86 be formed of a stiff, yet flexible material so as to give support to the body part that is greater than a flexible fabric yet which permits some flexing especially where used in conjunction with a bone and joint. In essence, strips 82, 84 and 86 provide auxiliary ligaments externally located to the body part. As external ligaments, these strips provide a load transference across the joint. While strips 82, 84 and 86 may be constructed of plastic (e.g. polyethylene) or other stiff, flexible materials, such as Teflon it is preferred that these strips be constructed of a composite material. As external ligaments, these strips conform to the shape of the outer surface of the body part during use. By being stiff yet resilient, the strips may also act to produce a performance advantage for the user.

Preferably, a woven composite such as a carbon/Kevlar blend fabric is employed, and an example is that product known as CF331 sold by Advanced Composites Company. Kevlar is known to be a para-aramid fiber produced from poly-paraphenylene. It is preferred that two or three layers of this woven material are impregnated with a polyester resin and are then laminated to one another to increase thickness. A laminate layer may also include of a carbon/fiberglass blend weave such as that available from Knytex of Seguin, Tex. Naturally, as many laminate layers as desired are within the scope of this invention. A suitable resin for this purpose is an isoflex polyester resin such as that designated as product number 53609 from the Ashland Chemical Company of Columbus, Ohio. In addition to the carbon/Kevlar blends, a polyethylene fiber material such as that known as Spectra polyethylene fiber available from Allied-Signal, Inc., of Petersburg, Va. may be employed. These materials provide excellent support along with impact resistance and thus impact protection. In addition, these materials are lubricious so that, with the nylon sheath, fairly low friction occurs to allow the floating motion. As an alternative, one can use a Teflon coated material to construct the sheathes thereby achieving the desired low friction interface between the strip and the sheath.

Figure 9:
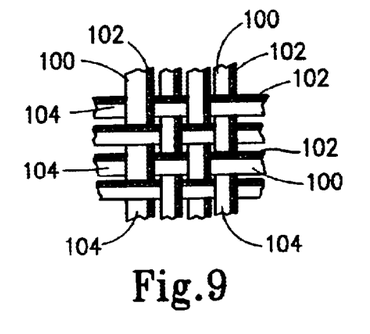
FIG. 9 is an enlarged front view in elevation of a portion of the woven elongated support piece used in the first exemplary embodiment of the present invention.

With reference, then, to FIG. 9, the preferred carbon/Kevlar blend fabric layer is shown. Here, a Kevlar strand 100 is an aramid material and is placed along a strand 102 of graphite to form a combination thread 104. Threads 104 are then woven in a standard manner to produce a stiff yet flexible strip that is extremely thin in dimension and which may be impregnated with a resin to enhance its stiffness properties, to further retain the woven threads 104 together and to laminate to another such layer. By being extremely thin yet strong, the combination of the nylon sheath with the strip is very thin to enhance the ability to conceal the brace during use, for example, under clothing. Such reduced dimension of thickness also allows the brace to be used inside a person's shoe where the brace is used on the ankle or foot. Moreover, the impregnated Kevlar/graphic strip is relatively slippery with respect to the nylon sheath so that the longitudinal and lateral movement when the sheath is not impeded. In addition, if desired, coatings can be placed on the strips to improve their efficiency. This coating can be a hydrophobic coating such as Vellox 140 manufactured by M-Chem Corporation of Wilmington, Mass. These coatings act to repel water or sweat from the strips.

As noted above, the present invention can be employed to construct a variety of braces. While brace 10 is shown to be constructed independently of either elastic support 16 or elastic support 116, thereby to form a brace system, it is also within the scope of this invention to permanently affix brace 10 to the elastic support thereby to provide a combination brace. Moreover, as noted above, it is possible to construct the brace according to the present invention so as to support different parts.

Figure 11:
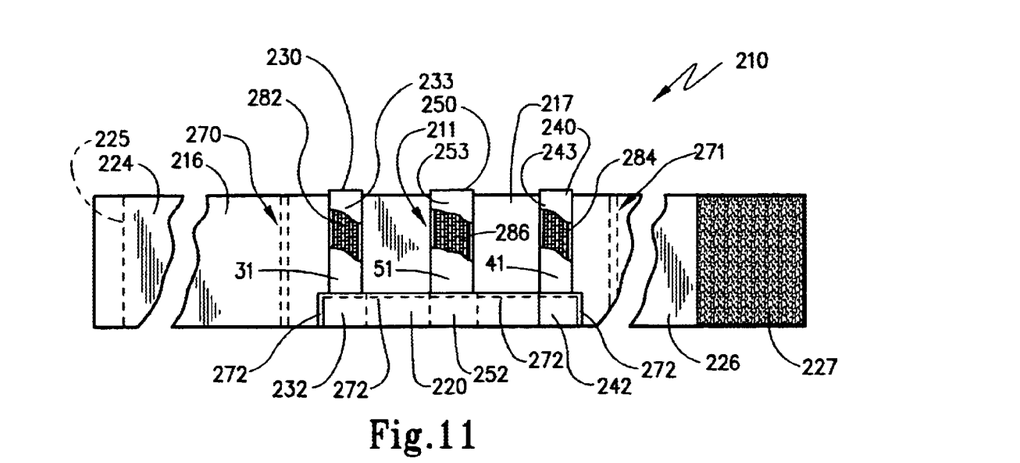
FIG. 11 is a front view in elevation of a second exemplary embodiment of the present invention, in this case, in the form of a back brace.

Thus, for illustrative purposes of both of these alternative approaches, FIG. 11 shows a combination back brace 210 that includes a support web 216 that is adapted to extend around the mid-section of a person's body. Support web 216 includes a medial portion 217 formed of a flexible yet substantially elastic fabric. Elastic webs 224 and 226 extend oppositely one another and are fastened to medial portion 217 at stitching 270 and 271, respectively. Elastic webs 224 and 226 are provided with mating hook and loop fasteners such as fill-a-form elements 225 (shown in phantom) and loop elements 227. The dimension of loop elements 227 selected so as to provide some degree of adjustment based on the attachment location of fill-a-form elements 225 to loop elements 227 when support web 216 encircles the torso.

In any event, brace section 211 is secured to flexible web 217. Here, sleeve portion 220 of brace section 211 may be sewn to flexible web 217 at stitching 272 to secure the first end portions 31, 41, and 51 to flexible web 217 at junction locations 232, 242 and 252, respectively. Here, again, strips 282, 284 and 286 are received in the respective interior of sheaths 230, 240 and 250 and are sized for relative movement therein. Second end portions 233, 243 and 253 of sheaths 230, 240 and 250 are free so that sheaths 230, 240 and 250 are not attached along to web 217 along their length except at junctions 232, 242 and 252.

From the above description, it should be appreciated that brace system 210 may support the lower back of a person along the long axis of the spine with sheath 250 oriented over the spine while sheath 230 and 240 are located parallel to the spine on opposite sides thereof.

Figure 12:
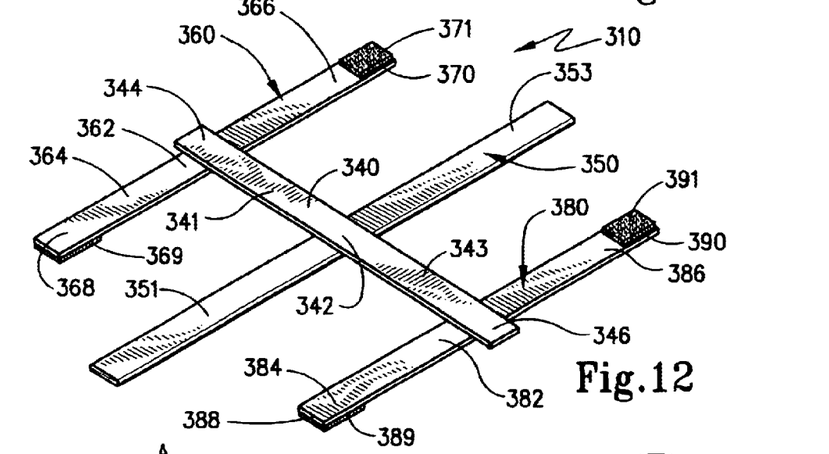
FIG. 12 is a perspective view of a third exemplary embodiment of the present invention, here, in the form of an ankle brace.
Figure 13:
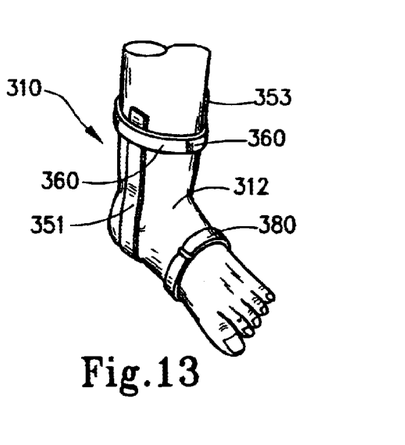
FIG. 13 is a perspective view of the ankle brace of FIG. 12 mounted around the ankle of a human foot.
Figure 14:
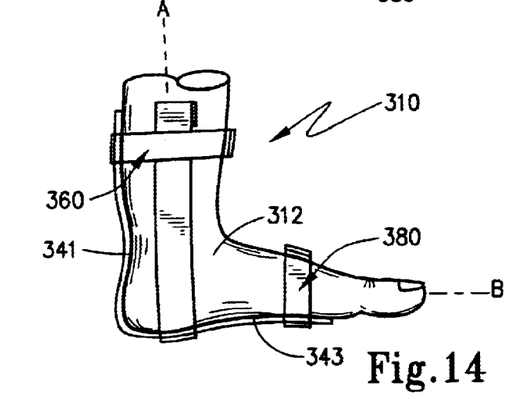
FIG. 14 is a side view in elevation showing the mounting of the ankle brace of FIG. 12 around the human foot.

A second alternative embodiment of the present invention is shown in FIGS. 12–14. Here, brace 310 is adapted to be placed in a supporting state about the ankle 312 of a person. Brace 310 includes a pair of sheaths 340 and 350 which are orthogonal to one another and which are secured to each other at a junction 342. Each of sheaths 340 and 350 receive a stiff yet resilient strip of laminated construction discussed above. Moreover, these strips (not shown) are mounted for floating movement within each of sheaths 340 and 350 as should now be fully appreciated from the above description.

In any event, a first elastic strip 360 is secured at a first end portion 344 of sheath 340 and extends perpendicularly thereto so as to be parallel to sheath 350. Strip 360 is joined at medial portion 362 so as to have opposite end portions 364 and 366 that may be secured around the ankle, as is shown in FIGS. 13 and 14. To this end, ends 368 and 370 are respectively provided with mating filaform fasteners, that is, hook and loop fasteners 369 and 371. Similarly, a second elastic strip 380 is secured at its mid-portion 382 to a second end 346 of sheath 340. Elastic strip 380 is in spaced parallel relation to sheath 350 and has opposite end portions 384 and 386 that terminate in ends 388 and 390. Ends 388 and 390 are respectively provided with mating hook and loop fasteners 389 and 391. As is shown in FIGS. 13 and 14, elastic strip 380 can be extended around a mid-portion of the foot and fastened to secure brace 310 in position.

In use, then, the heal of the foot is placed over the junction 342 of sheaths 340 and 350. End portion 341 of sheath 340 (and its respective stiff strip) is configured to extend along side the back of the heal and ankle in the direction of long axis "A" and is fastened in that position by elastic strip 360. End portion 343 of sheath 340 extends underneath and along side the foot so as to extend parallel to the long axis "B" thereof. End portion 343 is secured by means of elastic strip 380. Prior to securing elastic strip 360, however, opposite end portions 351 and 353 of sheath 350 (and their associated strip portions) are bent upwardly along side the inner and outer portions of the ankle so as to be parallel to the long axis "A". End portions 351 and 353 are then secured by elastic strip 360 as shown in FIGS. 13 and 14. Due to their relatively thin dimensional thickness, the strips and sheaths forming brace 310 are relatively easy to conceal under a sock or other foot coverings and can be readily worn inside of a normal shoe or athletic footwear.

Figures 15, 16:
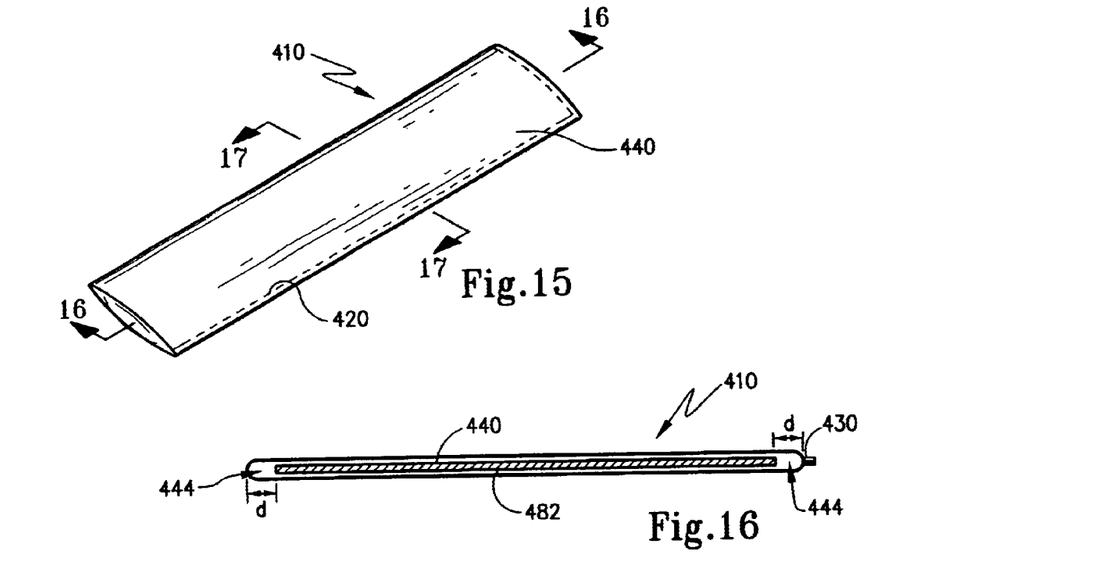
FIG. 15 is a perspective view of a splint according to the present invention.
FIG. 16 is a cross-sectional view taken about lines 16—16 of FIG. 15.

A fourth alternative embodiment of the present invention is shown in FIGS. 15–16. Here, the invention is in the form of a splint 410 that includes a sheath 440 formed out of a flexible slick fabric, such as nylon so as to have an interior 444. Sheath 440 receives a stiff yet resilient strip 482 in the interior 444 thereof with strip 482 preferably being of the laminated construction discussed above. As may be best seen in FIG. 16, the length of strip 482 is slightly less than the length of sheath 440 so that an open region having a length "d" is formed at each end between the ends of strip 482 and sheath 440. Thus, strip 482 can slide or "float" longitudinally relative to sheath 440. Splint 410 is formed by producing a pocket of material by forming an overlapped portion of material with the edges thereof secured by stitching, such as shown at 420. Strip 482 is then inserted into the interior 440 and the end is sealed, such as stitching, as is shown at 430.

Figures 17, 19:
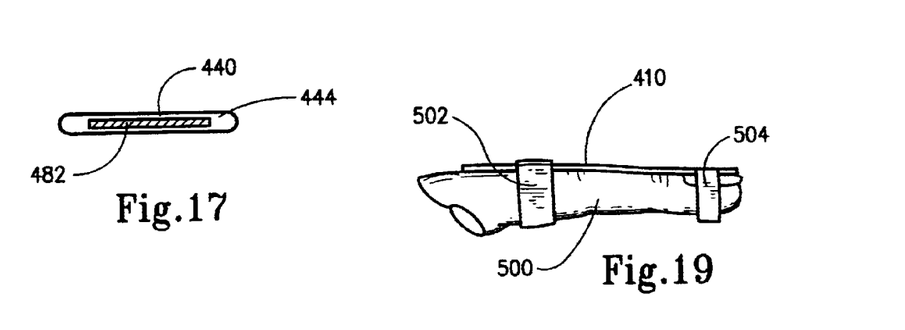
FIG. 17 is a cross-sectional view taken about lines 17—17 of FIG. 15.
FIG. 19 is an exploded view in perspective showing three splints of FIGS. 15–17 arranged to protect a human forearm.
Figure 18:
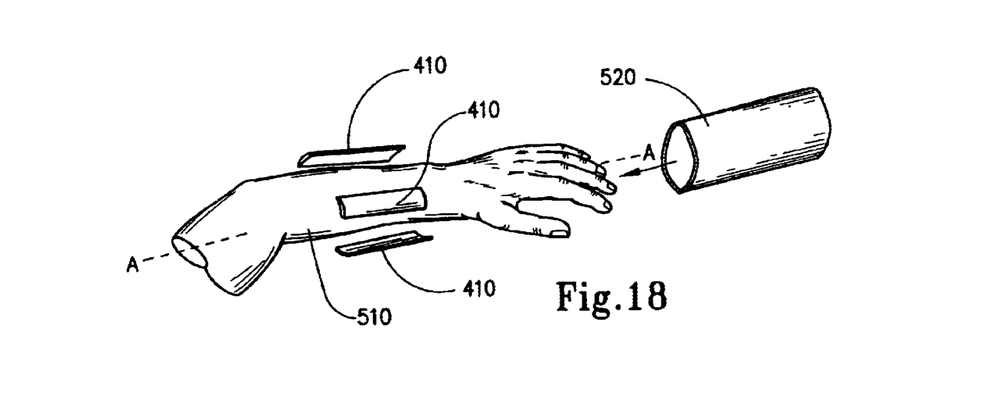
FIG. 18 is a side view in elevation showing the splint of FIGS. 15–17 protecting a human finger.

Splint 410 is very versatile in use. For example, as is shown in FIG. 19, splint 410 can be used to support a human finger 500. To this end, splint 410 is placed over the top of finger 500 and is secured by adhesive strips 502 and 504 extending around the finger. In an alternative use, a plurality of splints 410 can be placed parallel to the long axis "A" of a forearm 510 of a human arm and equiangularly spaced therearound, if desired. An elastic sleeve 520 can then be telescopically received over the forearm 510 to hold splints 410 in position, as is shown in FIG. 18.

The present invention finally is directed to a method that is accomplished by the structures described above. Therefore, the method of the present invention externally supports a selected body part having a long axis. The method includes a first step of providing a splint that includes a sheath of flexible material and a support piece disposed in the interior of the sheath. Next, the method includes the step of placing the splint alongside the selected body part in an orientation that is parallel to the long axis thereof. Finally, the splint is secured in a mounted state in a manner such that, during movement, the support piece can reciprocate in a longitudinal direction within the interior of the sheath.

The method also may include the step of providing a plurality of these splints, placing each of the splints alongside the selective body part in an orientation that is parallel to the long axis and securing each of the splints in a mounted state, in a manner such that, during movement, each support piece can reciprocate in a longitudinal direction within the interior of its respective sheath. The method can also include the step of orienting the splints in spaced-apart relation to one another, and this method can also include equiangularly spacing of the splints around the selected body part. The step of securing the splint can be accomplished by utilizing a non-stretchable mounting strip extending around the selected body part or, alternatively, utilizing a mounting strip that includes an elastic portion.

From the foregoing, it should be appreciated that a variety of constructions and materials may be used for forming the support brace and splints according to the teachings of the present invention. Therefore, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A brace adapted for use on a body to externally support a selected body part having a long axis, comprising:

(a) a mounting piece operative to releasably secure in a mounted state to a portion of the body at a location proximate to the selected body part;

(b) an elongated sheath formed of a first flexible material and having a sheath interior with a first length and including a first sheath end connected at a junction to said mounting piece and a second sheath end opposite said first sheath end; and (c) an elongated flat support piece formed of a composite material comprising two different fibers woven together and impregnated with a flexible, cured resin such that said support piece is stiff, yet flexible, said support piece being received in the sheath interior and having a second length that is less than the first length whereby said support piece may move relative to said sheath within the interior thereof, said sheath and said support piece configured to extend alongside the selected body part when in the mounted state.

2. A brace according to claim 1 including a plurality of sheaths each formed of a first flexible material and having a sheath interior with a first length and including a first sheath end connected at a junction to said mounting piece and a second sheath end opposite said first sheath end and including a plurality of support pieces each formed of a composite material comprising two different fibers woven together and impregnated with a flexible, cured resin such that each support piece is stiff, yet flexible, each said support piece being received in the sheath interior of a respective one of said sheaths, each said support piece having a second length that is less than the first length whereby said support piece may move relative to its respective said sheath within the interior thereof.

3. A brace according to claim 2 wherein said mounting piece is inelastic between the junctions.

4. A brace according to claim 1 wherein the composite material is selected from a group consisting of aramid compounds, graphite and plastic.

5. A brace according to claim 1 wherein said support piece is constructed of a carbon/aramid fiber blend.

6. A brace according to claim 1 wherein said support piece is coated with a hydrophobic material.

7. A splint adapted for use on a body to externally support a selected body part having a long axis, comprising:
(a) an elongated sheath formed of a flexible material and having a sheath interior with a first length; and
(b) an elongated flat support piece formed of a composite material comprising two different fibers woven together and impregnated with a flexible, cured resin such that said support piece is stiff, yet flexible, said support piece being received in the sheath interior and having a second length that is less than the first length whereby said support piece may move relative to said sheath within the interior thereof, said sheath and said support piece configured to extend alongside the selected body part when in the mounted state.

8. A splint according to claim 7 wherein the composite material is selected from a group consisting of aramid compounds, graphite and plastic.

9. A splint according to claim 7 wherein said support piece is constructed of a carbon/aramid fiber blend.

10. A splint according to claim 7 wherein the flexible material is a nylon fabric.

11. A splint according to claim 7 including a mounting piece operative to releasably secure said sheath and said support piece to a portion of the body alongside the selected body part and parallel to a long axis thereof.

12. A system adapted for use on a body to externally support a selected body part having a long axis, comprising:
(a) a mounting piece operative to releasably secure in a mounted state to a portion of the body at a location proximate to the selected body part;
(b) an elongated sheath formed of a flexible material and having a sheath interior with a first length and including a first sheath end connected to said mounting piece and a second sheath end opposite said first sheath end;
(c) an elongated support piece formed of a stiff material and received in the sheath interior and having a second length that is less than the first length whereby said support piece may move relative to said sheath within the interior thereof, said sheath and said support piece configured to extend alongside the selected body part when in the mounted state; and
(d) an elastic casing separate from and independent of said mounting piece, said casing sized and adapted to extend over the selected body part in a retaining position and operative in the retaining position to encase a major portion of said sheath and said support piece when in the mounted state.

13. A brace according to claim 12 including a plurality of sheaths each formed of a first flexible material and having a sheath interior with a first length and including a first sheath end connected at a junction to said mounting piece and a second sheath end opposite said first sheath end and including a plurality of support pieces each formed of a stiff material and received in the sheath interior of a respective one of said sheaths, each said support piece having a second length that is less than the first length whereby said support piece may move relative to its respective said sheath within the interior thereof, said casing sized and adapted to mount each of said sheathes alongside the selected body part.

14. A brace according to claim 13 wherein said sheaths are in parallel spaced relation to one another.

15. A brace according to claim 12 wherein said support piece is constructed of a composite material.

16. In an elastic brace adapted for use on a body to externally support a selected body part having a long axis wherein the brace includes an elastic casing sized and adapted to extend around and encase the selected body part, the improvement comprising an elongated sheath formed in said casing and constructed of a flexible material and having a sheath interior with a first length and an elongated, flat support piece constructed as a woven composite comprising a carbon/aramid fiber and resin blend that is stiff, yet flexible after curing, said support piece being received in the sheath interior and having a second length that is less than the first length whereby said support piece may move relative to said sheath within the interior thereof.

17. A method for externally supporting a selected body part having along axis, comprising the steps of:
(a) providing a plurality of splints each including a sheath of flexible material and a support piece disposed in an interior of said sheath;
(b) placing each of said splints alongside the selected body part in an orientation that it parallel to the long axis thereof; and
(c) securing each said splint in a mounted state utilizing a non-stretchable mounting strip extending around a portion of the selected body part in a manner such that, during movement, each said support piece can reciprocate in a longitudinal direction within the interior of said sheath.

18. The method according to claim 17 including the step of orienting said splints in spaced-apart relation to one another.

19. The method according to claim 18 wherein said splints are placed in equiangularly spaced relation around the selected body part.

20. The method according to claim 17 wherein the step of securing said splint is accomplished by utilizing a mounting strip that extend completely around the selected body part and wherein said mounting strip includes an elastic portion.

21. A brace adapted for use on a body to externally support a selected body art having a long axis, comprising:
(a) a mounting piece operative to releasably secure in a mounted state to a portion of the body at a locatiob proximate to the selected body part, said mounting piece including a flexible, inelastic portion;
(b) a plurality of sheaths each formed of a first flexible material, each said sheath having a sheath interior of a first length and including
(1) a first sheath end connected at a junction to the inelastic portion of said mounting piece and
(2) a second sheath end opposite said first sheath end with said junctions being spaced-apart from one another; and
(c) a plurality of flat support pieces each formed of a stiff material and received in the sheath interior of a respective one of said sheaths, each said support piece having a second length that is less than the first length whereby said support piece may move relative to its respective said sheath within the interior thereof.

22. A brace according to claim 21 wherein said mounting piece is constructed of the first flexible material.

23. A brace according to claim 21 wherein the first flexible material is nylon fabric.

24. A brace according to claim 21 wherein said mounting piece includes an elastic portion.

25. A brace according to claim 21 wherein said sheath interior has a first width and each said support piece has a second width that is less than the first width of its respective said sheath.

26. A brace according to claim 21 wherein each said support piece has a first end affixed to said mounting piece and a second end freely floating in said heath.

27. A brace according to claim 21 wherein one of said support pie es is of a different width than another of said support pieces.

28. A brace according to claim 21 wherein said sheaths are in parallel spaced relation to one another.

29. A brace according to claim 21 including three said sheaths and three said support pieces.

30. A brace according to claim 21 wherein said support piece is constructed of a composite material.

31. A brace according to claim 21 wherein said support piece is constructed of two different fibers woven together.

32. A brace according to claim 21, wherein said mounting piece is secured to an elastic casing, said casing sized and adapted to extend around the selected body part in a retaining position and operative in the retaining position to encase a major portion of each of said sheaths.

33. A brace adapted for use on a body to externally support a selected body part having a long axis, comprising:
    (a) a mounting piece operative to releasably secure in a mounted state to a portion of the body at a location proximate to the selected body part;
    (b) a plurality of sheaths each formed of a first flexible material and having a sheath interior with a first length and including a first sheath end portion connected at a junction to said mounting piece and a free second sheath end portion opposite said first sheath end portion; and
    (c) a plurality of support pieces each formed of a stiff material and received in the sheath interior of a respective one of said sheaths, each said support piece having a second length that is less than the first length whereby said support piece may move relative to its respective said sheath within the interior thereof;
    (d) an elastic casing sized and adapted to extend over the selected body part in a retaining position and operative in the retaining position to encase said mounting member and a major portion of each of said sheaths when in the mounted state.

34. T A brace according to claim 33 wherein each said support piece has a first end affixed to said mounting piece and a second end freely floating in said sheath.

35. A brace according to claim 33 wherein said mounting piece is inelastic between the junctions.

36. A brace according to claim 33 wherein said mounting piece is secured to said casing.

37. A brace according to claim 33 wherein said mounting piece is separate from and independent of said casing.

* * * * *

UNITED STATES PATENT AND TRADEMARK OFFICE
CERTIFICATE OF CORRECTION

PATENT NO.   : 6,676,619 B2
DATED        : January 13, 2004
INVENTOR(S)  : Wayne R. Arden It is certified that error appears in the above-identified patent and that said Letters Patent is hereby corrected as shown below:

Column 5,
Line 12, "18" should read -- 19 --;
Line 14, "19" should read -- 18 --;

Column 12,
Line 55, "locatiob" should read -- location --;

Column 13,
Line 19, "pie es" should read -- pieces --.

Signed and Sealed this

Fourteenth Day of September, 2004

JON W. DUDAS
*Director of the United States Patent and Trademark Office*